(12) United States Patent
Barata et al.

(10) Patent No.: US 11,377,472 B2
(45) Date of Patent: Jul. 5, 2022

(54) METHOD FOR FRACTIONATING SOLUBLE FRACTIONS OF PEAS, FRACTION THUS OBTAINED AND UPGRADE THEREOF

(71) Applicant: ROQUETTE FRERES, Lestrem (FR)

(72) Inventors: Manuel Barata, Gonnehem (FR); Pierrick Duflot, La Couture (FR); Claire Dhalleine, Compiegne (FR); Jean-Marc Verrin, Beuvry (FR)

(73) Assignee: ROQUETTE FRERES, Lestrem (FR)

( * ) Notice: Subject to any disclaimer, the term of this patent is extended or adjusted under 35 U.S.C. 154(b) by 107 days.

(21) Appl. No.: 14/764,748

(22) PCT Filed: Jan. 31, 2014

(86) PCT No.: PCT/FR2014/000023
§ 371 (c)(1),
(2) Date: Jul. 30, 2015

(87) PCT Pub. No.: WO2014/118449
PCT Pub. Date: Aug. 7, 2014

(65) Prior Publication Data
US 2015/0368293 A1    Dec. 24, 2015

(30) Foreign Application Priority Data

Jan. 31, 2013   (FR) ...................................... 1350853

(51) Int. Cl.
*C07K 1/34*       (2006.01)
*A23J 3/14*       (2006.01)
(Continued)

(52) U.S. Cl.
CPC ................... *C07K 1/34* (2013.01); *A23J 3/14* (2013.01); *B01D 61/16* (2013.01); *B01D 61/58* (2013.01);
(Continued)

(58) Field of Classification Search
None
See application file for complete search history.

(56) References Cited

U.S. PATENT DOCUMENTS 4,766,204 A    8/1988  Nickel
5,086,166 A    2/1992  Lawhon et al.
(Continued)

FOREIGN PATENT DOCUMENTS

FR    2 778 407 A1    11/1999
FR    2 889 416 A1    2/2007
(Continued)

OTHER PUBLICATIONS

Lawhon et al., "Fractionation and Recover of Cottonseed Whey Constituents by Ultrafiltration and Reverse Osmosis", Cereal Chem., 52 (1), Jan.-Feb. 1975, pp. 34-43.*
(Continued)

*Primary Examiner* — Elizabeth Gwartney

(57) ABSTRACT

A method for fractionating soluble fractions of peas, includes, in sequence, a step of microfiltering or centrifuging, followed by a step of ultrafiltering, and optionally a reverse-osmosis step. A reduction of the leakage of proteins toward the soluble fractions, an improvement of the yield of the single concentration step by evaporating the soluble fractions, and the selective isolation of proteins of interest are thus achieved. The method is easy to implement, the devices used at each single step are conventional and well known to the person skilled in the art. Also, the method does not use any organic solvent other than water.

12 Claims, 5 Drawing Sheets

(51) Int. Cl.
  *B01D 61/58* (2006.01)
  *B01D 61/16* (2006.01)
  *C07K 1/36* (2006.01)
  *C07K 14/415* (2006.01)
  *B01D 61/02* (2006.01)
  *B01D 61/14* (2006.01)

(52) U.S. Cl.
  CPC .............. *C07K 1/36* (2013.01); *C07K 14/415* (2013.01); *B01D 61/025* (2013.01); *B01D 61/145* (2013.01); *B01D 61/147* (2013.01); *B01D 2311/04* (2013.01); *B01D 2315/10* (2013.01)

(56) References Cited

U.S. PATENT DOCUMENTS

| | | | |
|---|---|---|---|
| 5,955,082 | A | 9/1999 | Bodnaryk et al. |
| 6,818,234 | B1 | 11/2004 | Nair et al. |
| 7,186,807 | B2 | 3/2007 | Freres |
| 2008/0226810 | A1 | 9/2008 | Freres |
| 2010/0263089 | A1 | 10/2010 | Delobel et al. |
| 2012/0034342 | A1 | 2/2012 | Freres |
| 2012/0121741 | A1 | 5/2012 | Delbaere |
| 2015/0184140 | A1 | 7/2015 | Freres |

FOREIGN PATENT DOCUMENTS

| | | |
|---|---|---|
| WO | 2006/052003 A1 | 5/2006 |
| WO | 2008105023 A1 | 9/2008 |
| WO | 2011082358 A1 | 7/2011 |
| WO | 2012/116703 A1 | 9/2012 |

OTHER PUBLICATIONS

Swanson et al., "Pea and Lentil Protein Extraction and Functionality"—JAOCS, vol. 67, No. 5, 1990, pp. 276-277. (Year: 1990).*
Woodard et al., "Bioseparation: Proteins", Encyclopedia of Agricultural, Food, and Biological Engineering, 2 Volume Set (2nd Edition)-bioprocessing of Fluids from Transgenic Animals. Taylor & Francis, (2010), p. 199. (Year: 2010).*
Naczk M., Rubin L.J., Shahidi F., Functional properties and phytate content of pea protein preparations. Journal of Food Science, vol. 51, No. 5, 1986, p. 1245-1247.
Sumner A.K., Nielsen M.A., Youngs C.G., Production and evaluation of pea protein isolate. Journal of Food Science, vol. 46, 1981, p. 364-372.
International Search Report, dated Apr. 14, 2014, from corresponding PCT Application.
Lei (Leigh) Gao et al., "Pilot Scale Recovery of Proteins from a Pea Whey Discharge by Ultrafiltration", LWT—Food Science and Technology, vol. 34, No. 3,May 1, 2001 (May 1, 2001), pp. 149-158, XP055076942, ISSN:0023-6438, 10.1006/fstl.2000.0743, cited in the application, abstract, pp. 149, 150; pp. 154, 155, p. 157.
Kuo, Alice, "Management of Effluents From Field Pea Wet Milling Process Using Ultrafiltration Technology," Food Science Department, University of Manitoba, Winnipeg, Manitoba, Master of Science Thesis submitted May 2000.
The English translation of the Preliminary Opinion by the Opposition Division of the EPO, dated Sep. 6, 2019, in the related European Application No. 14706872.0.
"Basics of Spiral Wound Ro Membranes Reverse Osmosis(Ro) Factsheet", Water Quality Association, (20130000), URL: https://www.wqa.org/Portals/0/Technical/Technical%20Fact%20Sheets/2016_RO. adf.
Boye et al., "Pulse proteins: Processing, characterization, functional properties and applications in food and feed", Food Research International (20100000), vol. 43, pp. 414-431.
Boye et al, "Protein Processing in Food and Bioproduct Manufacturing and Techniques for Analysis", Food and Industrial Bioproducts and Bioprocessing, 2012, pp. 85-104.
Cheryan M., "membranes properties", Ultrafiltration and Microfiltration Handbook, 1998, pp. 104-147.
"Cross-flow filtration", Wikipedia, pp. 1-4, URL: https://en.wikipedia.org/wiki/Cross-flow_filtration.
Cui et al., "Membrane Technology—A Practical Guide to Membrane Technology and Applications in Food and Bioprocessing," , ISBN 978-1-85617-632-3.
"Filtration membranaire (OI, NF, UF, MFT)—Aspects théoriques: meçanismes de transfert (J2789V1", Techniques de 'Ingęnieur, Feb. 10, 2010. (The English abstract included. ).
Fuhrmeister et al., "Impact of processing on functional properties of protein products from wrinkled peas", J. Food Eng., 2003, vol. 56, pp. 119-129.
Higgins et al., "Gene Structure, Protein Structure, and Regulation of the Synthesis of a Sulfur-rich Protein in Pea Seeds", The Journal Of Biological Chemistry, 1986, vol. 261, No. 24, pp. 11124-11130.
Lawhon et al., "Combining aqueous extraction and membrane isolation techniques to recover protein and oil from soybean", J. Food Sci., 1981, vol. 46, pp. 912-919.
Lawhon et al., "Fractionation and Recovery of Cottonseed Whey Constituents by Ultrafiltration and Reverse Osmosis", Cereal Chem., 1975, vol. 52, pp. 34-43.
"Protein Concentration and Diafiltration by Tangential Flow Filtration", Millipore brochure, 2003, pp. 1-24.
Vose, J.R., "Production and functionality of starches and protein isolates from legume seeds (field peas and horsebeans)", Cereal Chem., 1980, vol. 57, pp. 406-410.
Leboucher et al., "A Swarm Intelligence Method Combined to Evolutionary Game Theory Applied to the Resources Allocation Problem", International Journal of Swarm Intelligence Research, (2012), vol. 3, pp. 20-38.
D30 "Mikrofiltration", "Ultrafiltration"; "Membranfiltration", "Umgekehrte Osmose", Jürgen Falbe, Römpp, Chemistry Lexicon, 1991.
D31 "Ultrafiltration", Institut—National Polytechnique(INP), pp. 1-17, Sep. 2015. (Only English translation of the relevant portion.).
D32 : H. Fuhrmeister et al, "Production of protein products based on a process for starch production from peas", Dissertation, Bedin, 2001, (English translation of the Relevant Portions).
D33: Ehlers, Meuser et al, "Market opportunities of marker pea starch, final report of scientific study," Munster, 1997, (English translation of the relevant portions).
D22 : "chapter 2", Daufin et al, Membrane separations in food industry processes, 1998, (English translation of the relevant portions).
D35. Perrot, "Pea proteins: from their function in the seed to their use in food animal," INRA Productions Animates, 1995, 8 (3), pp. 151-164. (English translation of the relevant portion).
D37. Lenntech BV, "GE Osmonics Desal membranes," Lenntech, Dec. 10, 2019.
D40. Belitz, W. Grosch, P. Schieberle, Food Chemistry, 4th revised edition, Springer 2009 , p. 62, "partial thermal denaturation".
D41. "Phytinsaure", Römpp, Chemistry Lexicon, 1998. (English translation of the relevant portion).
D42 : Rimbach/Möhring—Lebensmittel-Warenkunde für Einsteiger; insbes. S. 155-160—a summary of university lectures in Kiel for Oecotrophology, 2010. (English translation of the relevant portions).
D43 : Food Toxicology, Machholz etc. page 244: Phytinsäure, 1989. (English translation of the relevant portions).
D23 "Principes de base de la filtration membranaire" by Patrice Bacchin, publically available on Jan. 2, 2008 (Partial English translation only).

* cited by examiner

METHOD FOR FRACTIONATING SOLUBLE FRACTIONS OF PEAS, FRACTION THUS OBTAINED AND UPGRADE THEREOF

CROSS-REFERENCE TO RELATED APPLICATION

This application is a U.S. national stage application of International patent application No. PCT/FR2014/099923, filed Jan. 31, 2014, which claims the priority of French application No. 1350853, filed Jan. 31, 2013, the subject matter of PCT/FR2014/099923 being incorporated in its entirety by reference herein.

The present invention relates to an original method for fractionating pea soluble fractions, comprising a microfiltration or centrifugation step, followed by an ultrafiltration step, and an optional reverse osmosis step. A reduction in the leakage of proteins to the soluble fractions, an improvement in the yield of the unitary step of concentration by evaporation of the soluble fractions and the selective isolation of proteins of interest are thus achieved. It is also a method that is easy to implement, the devices used at each unitary step being conventional and well known to those skilled in the art.

Since the 1970's, the pea has been the leguminous seed plant which has been most widely developed in Europe and mainly in France, in particular as a protein source for animal feed, but also for food for human consumption. The pea contains approximately 27% by weight of protein matter. The term "pea" is herein considered in its broadest acceptance and includes in particular all the wild-type varieties of "smooth pea" and all the mutant varieties of "smooth pea" and of "wrinkled pea", regardless of the uses for which said varieties are generally intended (food for human consumption, animal feed and/or other uses).

Among the constituents of the pea, those which are currently most exploited are the starch, the fibers and the proteins, also referred to as noble constituents. The corresponding method of exploitation consists in initially preparing a starch milk, by mixing pea flour and water in a kneading machine. After having extracted the starch and the fibers from this milk, a protein-rich product is obtained. A flocculation operation is then carried out on the milk, in particular by thermocoagulation, the objective of which is to make the protein(s) of interest insoluble. At this stage of the method, it is necessary to carry out a separation, in particular by centrifugal decanting, so as to isolate a highly protein-rich composition also called "floc". The supernatant constitutes what those skilled in the art generally refer to as "soluble fractions".

It should first of all be specified that the term "soluble fractions" constitutes a misuse of language in the sense that said fraction contains a certain number of insoluble particles, such as various and varied colloids, but also and especially proteins. These soluble fractions must first of all be concentrated by evaporation, in such a way that the insoluble substances (and in particular the proteins) that they contain can be recovered. At the current time, the soluble fractions are exploited very little; they are used virtually exclusively as nitrogen source in fermentation and as nutritive feed for livestock once said fractions have been enriched with fibers.

The applicant has recently protected, through French patent applications No. 09 51962 and No. 12 57680, a method for extracting P-amylases from a soluble fraction from a starch plant, including the pea, said method comprising a step of clarification by microfiltration and a step of concentration/purification by ultrafiltration.

As it happens, it must be noted that the overall yield of the method leading from the initial pea to the protein-rich composition (the floc) is far from reaching 100%. It is considered that, at an industrial level, between 5% and 25%, but more generally around 20%, by weight of the proteins initially contained in the starting pea are found in the soluble fractions. This massive leakage of proteins, via the soluble fractions, raises a certain number of drawbacks.

The first of them is a dead loss of proteins of interest, which are currently only exploited through the protein floc resulting from the decanting step. If an overall isolation of the portion of proteins contained in the soluble fractions was achieved, said portion could advantageously be incorporated or redirected into the protein floc, with a view to enriching it.

The second problem raised by the method as it currently exists is a very mediocre yield at the level of the unitary step of concentration by evaporation of the soluble fractions: the rich protein content therein is such that the evaporator fouling phenomenon is very significant and requires frequent interruptions for cleaning. Indeed, by virtue of their heat sensitivity, proteins coagulate and have a predisposition to fouling the evaporation devices.

Finally and according to a third perspective, recent studies have shown that a portion of the proteins derived from the soluble fraction (the fraction termed PA1b) can be advantageously used in the production of an insecticide: this results from the teaching of document FR 2 778 407 A1. There is therefore also a technical advantage in selectively isolating one or more protein fractions actually within the soluble fractions.

To the applicant's knowledge, this problem has never been addressed as a whole, i.e. with a view to finding solutions aimed at solving the triple technical problem as stated above. The document "Pilot scale recovery of proteins from a pea whey discharge by ultrafiltration" (Lei (Leigh) Gao, Khai D. Nguyen and Alphonsus C. Utioh, Lebensm.-Wiss. u.-Technol., vol. 34, pp. 149-158, 2001) focuses on the recovery of the pea proteins by centrifugation followed by ultrafiltration. Patent application WO 2006/052003, for its part, relates to a method for preparing soluble polypeptides derived from a liquid effluent from pea conversion, by membrane filtration and then drying.

Working to find an overall solution for optimizing the yield of the method for extracting proteins from pea, the applicant has succeeded in developing a method which solves the triple technical problem:

of reducing the leakage of proteins to the soluble fractions, of improving the yield of the unitary step of concentration by evaporation of the soluble fractions, of selectively isolating the proteins of interest within the soluble fractions.

This method is based on the succession of various steps of separating said soluble fractions, a) by means of centrifugation or of microfiltration, b) then ultrafiltration, c) and, finally, optionally reverse osmosis.

Entirely advantageously, the implementation of these steps in a sequenced manner makes it possible, at the level of each filtration unit, to isolate a protein fraction of interest. Typically, the globulins and phytic acid are recovered in the microfiltration retentate or the centrifugation pellet (or sediment). The microfiltration permeate or the centrifugation supernatant then undergoes an ultrafiltration step: albumins then constitute most of the solids of the ultrafiltration retentate, the permeate being intended to undergo the optional reverse osmosis step. The latter makes it possible to isolate, on the one hand, a fraction rich in o-galactoside-type carbohydrates in the retentate, and, on the other hand, the amino acids, carbohydrates and other salts present in the permeate. Reference may be made to the diagram of the principle process illustrated in FIG. 1 of the present application, as well as FIGS. 2-5.

DETAILED DESCRIPTION OF THE PREFERRED EMBODIMENTS

Figure 1:
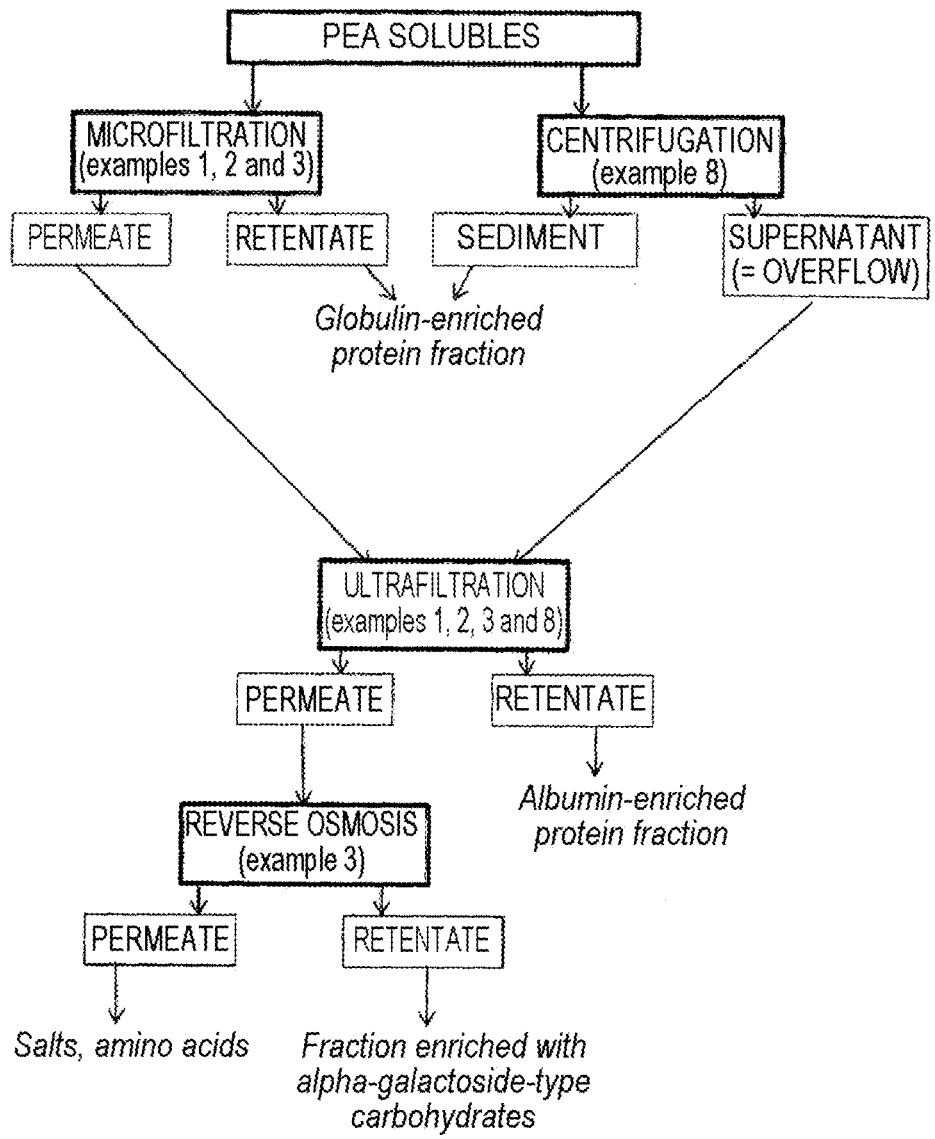
FIG. 1 illustrates the principle process in accordance with the disclosed invention.

The other FIGS. 2 to 5 illustrate the results and an electrophoretic profile obtained in the tests exemplified in the present application.

A very precise isolation of various categories of proteins of interest, which can subsequently be exploited in a given application, is thus achieved. Entirely advantageously, the microfiltration retentate and the sediment resulting from the centrifugation are rich in phytic acid. As it happens, this acid inhibits the absorption of various cations (Zn, Cu, Co, Mn, Ca, Fe) by forming insoluble salts (phytates). This property is exploited in enology: treatment with calcium phytate is the only one which is authorized (in France) for removing iron from red wines.

Likewise advantageously, the retentate resulting from the reverse osmosis step is particularly rich in a-galactoside, but also in the fraction termed PA1b which has a direct application in the production of insecticides of entirely biobased origin (as disclosed in the abovementioned document FR 2 778 407). Furthermore, all or part of the fractions rich in the various proteins of interest, and obtained at the level of each unitary filtration step, can be redirected to the floc, downstream of the centrifugal decanting step. As a result, the rich protein content of the floc increases.

Finally, the final permeate resulting from the reverse osmosis step, which advantageously contains the amino acids, carbohydrates and other salts, particles of very small sizes, can easily be concentrated by means of an evaporator, without however causing clogging problems, which require production to be frequently stopped for cleaning operations, or even changing devices.

Thus, a first subject of the present invention consists of a method for treating pea soluble fractions, comprising:
a) a step of microfiltration or centrifugation of said soluble fractions resulting in a microfiltration permeate or a centrifugation supernatant,
b) followed by a step of ultrafiltration of the microfiltration permeate or of the centrifugation supernatant, resulting in an ultrafiltration permeate and an ultrafiltration retentate,
c) followed by an optional step of reverse osmosis of the ultrafiltration permeate resulting in a permeate and a retentate from the reverse osmosis.

One of the originalities of the present invention consists in subjecting the pea soluble fractions, compositions which are a priori non-noble, to a certain number of treatment steps with a view to exploiting their content. This type of method where unitary treatment steps are applied directly to the soluble fractions should be clearly distinguished from the prior art processes which may have recourse to these same individual steps, but with a view to treating:
either the pea proteins free of the soluble fractions with a view to purifying said pea proteins,
or these same pea proteins still loaded with soluble fractions and with a view precisely to carrying out a separation between proteins and soluble fractions.

The first step of the method according to the invention is therefore a microfiltration or centrifugation step a) which is carried out directly on the pea soluble fractions, as derived from the centrifugal decanting step. The objective of this step is in particular to isolate a globulin-rich protein fraction.

The microfiltration of the pea soluble fractions results in a microfiltration permeate and a microfiltration retentate. It is the permeate which is then treated in the subsequent ultrafiltration step b). The centrifugation of the pea soluble fractions results, for its part, in a centrifugation supernatant and a centrifugation sediment. It is the supernatant which is then treated in the subsequent ultrafiltration step b).

When the first step is a microfiltration, it is preferentially a tangential membrane microfiltration. More particularly, the tangential microfiltration is preferentially carried out with ceramic membranes having a porosity of 0.01 μm to 1 μm, preferentially of 0.05 μm to 0.5 μm.

Optionally, this first microfiltration or centrifugation step may be preceded by a step of flocculation of the insoluble particles contained in the starch plant soluble fraction, by any technique known, moreover, to those skilled in the art.

The second step of the method according to the invention consists of an ultrafiltration step b), carried out on the microfiltration permeate or on the centrifugation supernatant. It makes it possible to obtain, on the one hand, an albumin-rich ultrafiltration retentate and, on the other hand, a permeate rich in the fraction termed PAlb about which it has already been mentioned that it can be exploited in the production of insecticide. The permeate in its entirety can therefore be directly exploited for this insecticide application; it is not necessary to overly treat/separate it.

More particularly, it is recommended to carry out the ultrafiltration using membranes which have a cut-off threshold of between 0.1 and 0.5 μm, the transmembrane pressure being maintained below 4 bar.

Finally, the method according to the invention comprises a third step c) which remains optional, but which is preferentially performed: it is a reverse osmosis step carried out on the ultrafiltration permeate.

The applicant recommends performing this osmosis with membranes which have a cut-off threshold of between 100 Da and 500 Da.

The examples which follow make it possible to illustrate the application more clearly without, however, limiting the scope thereof.

EXAMPLES

Example 1

This example illustrates the effectiveness of combining microfiltration with ultrafiltration in order to obtain, firstly, a globulin-rich microfiltration retentate and, secondly, a carbohydrate-rich ultrafiltration permeate.

The pea soluble fraction is first of all produced. Pea flour is initially prepared by grinding shelled fodder peas in an Alpine hammer mill equipped with a 100 µm screen. 300 kg of flour containing 87% of solids are then soaked in water at the final concentration of 25% on a dry weight basis, at a pH of 6.5. 1044 kg of flour suspension containing 25% of solids (i.e., therefore, 261 kg of dry flour) are then introduced with 500 kg of water into a battery of hydrocyclones composed of 14 stages. It is fed with the flour suspension at stage No. 5. This separation results in the production of a light phase which corresponds to the outlet of stage No. 1. It consists of the mixture of proteins, internal fibers and soluble materials.

This light phase at the hydrocyclone outlet contains as a mixture (142 kg on a dry weight basis in total): the fibers (approximately 14.8% by weight, i.e. 21 kg on a dry weight basis), the proteins (approximately 42.8% by weight, i.e. 60.8 kg on a dry weight basis) and the soluble materials (approximately 42.4% by weight, i.e. 60.2 kg on a dry weight basis). This fraction has a solids content of 11.4%. The fiber separation is carried out on Westfalia centrifugal decanters used in an industrial potato-processing starch unit. The light phase at the centrifugal decanter outlet contains a mixture of proteins and soluble materials, whereas the heavy phase contains the pea fibers. The heavy phase contains 105 kg of fibers containing 20% of solids. It is noted that virtually all the fibers are indeed found in this fraction.

As for the protein and soluble material fraction, it contains 1142 kg of a mixture in solution of soluble materials and proteins (fraction containing 6% of solids). The flocculation of the proteins is carried out at their isoelectric point by adjusting the light phase at the centrifugal decanter outlet to a pH of 4.5 and heating to 50° C.

The proteins thus flocculated are left in a maturing tank for 10 minutes. After precipitation of the proteins, centrifugal decanting is carried out, which makes it possible to recover, after drying, sediment containing 56 kg of proteins (86% of N×6.25 on a dry weight basis) containing 93% of solids.

The process is carried out in this way until 2500 liters of pea solubles are obtained, the pH of which is adjusted to 7.0 by adding 50% sodium hydroxide. The temperature of the resulting suspension was brought to 70° C. The composition of the resulting suspension (SOLF_1) is given in Table 1.1.

TABLE 1.1

| | SOLF_1 | |
|---|---|---|
| Solids content | 2.5 | g for 100 g |
| Protein content (N × 6.25) | 27 | g for 100 g of solids |
| Ash content | 16 | g for 100 g of solids |
| Total carbohydrate content of which: | 47 | g for 100 g of solids |
| Raffinose | 4.0 | g for 100 g of solids |
| Stachyose | 13.4 | g for 100 g of solids |
| Verbacose | 15.1 | g for 100 g of solids |
| Others | 10 | g for 100 g of solids |

The solution is pumped through a microfiltration unit equipped with Inside Ceram® ceramic membranes having a cut-off threshold of 0.14 µm (19 channels of 4.5 mm). Throughout the filtration, the temperature is regulated at 60° C. and the transmembrane pressure is maintained at a value of between 0.4 and 0.6 bar.

707 liters of microfiltration permeate (P014_1) and 1768 liters of microfiltration retentate (R014_1) are thus recovered. The compositions of each of the fractions are given in Table 1.2.

TABLE 1.2

| | P014_1 | R014_1 | |
|---|---|---|---|
| Solids content | 2.5 | 2.5 | % |
| Protein content (N × 6.25) | 26.5 | 27.2 | g/100 g of solids |
| Ash content | 21.0 | 14.0 | g/100 g of solids |
| Total carbohydrate content | 45.0 | 47.0 | g/100 g of solids |
| Others | 7.5 | 11.8 | g/100 g of solids |

550 liters of the permeate (P014_1) are pumped through an ultrafiltration unit. The ultrafiltration unit is equipped with Kerasep® BX ceramic membranes sold by the company Novasep and having a cut-off threshold of 15 kDa (7 channels of 6 mm). Throughout the filtration, the temperature is regulated at 60° C. and the transmembrane pressure is maintained at a value of between 1 and 3 bar.

467 liters of ultrafiltration permeate (P15_1) and 33 liters of retentate (R15_1) are thus recovered. The compositions of each of the fractions are given in Table 1.3.

TABLE 1.3

| | P15_1 | R15_1 | |
|---|---|---|---|
| Solids content | 2.2 | 7.2 | % |
| Protein content (N × 6.25) | 15.0 | 75.1 | g/100 g of solids |
| Ash content | 23.6 | 10.3 | g/100 g of solids |
| Total carbohydrate content | 52.6 | 12.5 | g/100 g of solids |
| Others | 8.8 | 2.1 | g/100 g of solids |

Example 2

In comparison with the previous example, this example illustrates the benefit of diafiltration for optimizing the richness of the retentate.

600 liters of pea solubles resulting from an isoelectric coagulation process are adjusted to a pH of 7.0 by adding 50% sodium hydroxide. The temperature of the resulting suspension was brought to 60° C. The composition of the suspension is the one given in Table 1.1 above.

The solution is pumped through a microfiltration unit equipped with Inside Ceram® ceramic membranes having a cut-off threshold of 0.14 µm (19 channels of 4.5 mm). Throughout the filtration, the temperature is regulated at 60° and the transmembrane pressure is maintained at a value of between 0.4 and 0.6 bar.

160 liters of microfiltration permeate (P014_2) and 400 liters of microfiltration retentate (R014_2) are thus recovered.

110 liters of the permeate (P014_2) are pumped through an ultrafiltration unit. The ultrafiltration unit is equipped with Kerasep® BX ceramic membranes sold by the company Novasep and having a cut-off threshold of 15 kDa (7 channels of 6 mm). The retentate fraction is maintained in total recycling on the feed and the permeate is discharged. The feed is supplemented with a permanent flow of water in a proportion of one volume of water for 7 volumes of permeate discharged. Throughout the filtration, the temperature is regulated at 60° C. and the transmembrane pressure is maintained at a value of between 2 and 3 bar.

107 liters of ultrafiltration permeate (P15_2) and 7 liters of retentate (R15_2) are thus recovered. The retentate (R15_2) is spray-dried. The composition of the fractions analyzed is given in Table 2.1.

TABLE 2.1

|  | P15_2 | R15_2 |  |
|---|---|---|---|
| Solids content | 3.3 | 11.0 | % |
| Protein content (N × 6.25) | 15.8 | 81.7 | g/100 g of solids |
| Ash content | 20.4 | 10.3 | g/100 g of solids |
| Total carbohydrate content | 51.0 | 6.8 | g/100 g of solids |
| Others | 12.8 | 1.2 | g/100 g of solids |

Example 3

This examples illustrates the beneficial effect of reverse osmosis for demineralizing and increasing the concentration of total carbohydrates of interest of the ultrafiltration permeate.

150 liters of pea solubles are treated according to the protocol described in example 2. 60 liters of ultrafiltration permeate (P15-3) are thus obtained and then pumped through a reverse osmosis unit equipped with Osmonics Desal® spiral organic membranes sold by General Electric Company and having a cut-off threshold of 350 Da. The retentate fraction is maintained in total recycling on the feed and the permeate is discharged. Throughout the filtration, the temperature is regulated at 50° C. and the pressure is maintained at a value of about 20 bar.

5 liters of retentate (R350_3) are thus recovered. The composition of the various fractions is given in Table 3.1.

TABLE 3.1

|  | P15_3 | R350_3 |  |
|---|---|---|---|
| Solids content | 2.2 | 14 | g/100 g |
| Protein content (N × 6.25) | 14.5 | 9 | g/100 g of solids |
| Ash content | 20 | 6 | g/100 g of solids |
| Total carbohydrate content | 56 | 65 | g/100 g of solids |
| Raffinose | 4.5 | 6.0 | g/100 g of solids |
| Stachyose | 18.0 | 19.1 | g/100 g of solids |
| Verbacose | 16.9 | 21.0 | g/100 g of solids |
| Others | 16.5 | 12.0 | g/100 g of solids |

Example 4

The solubility as a function of the pH of the spray-dried fraction R15_2 obtained in example 2 is measured. It is compared to that of a Nutralys® F85M pea protein isolate sold by the applicant.

Figure 2:
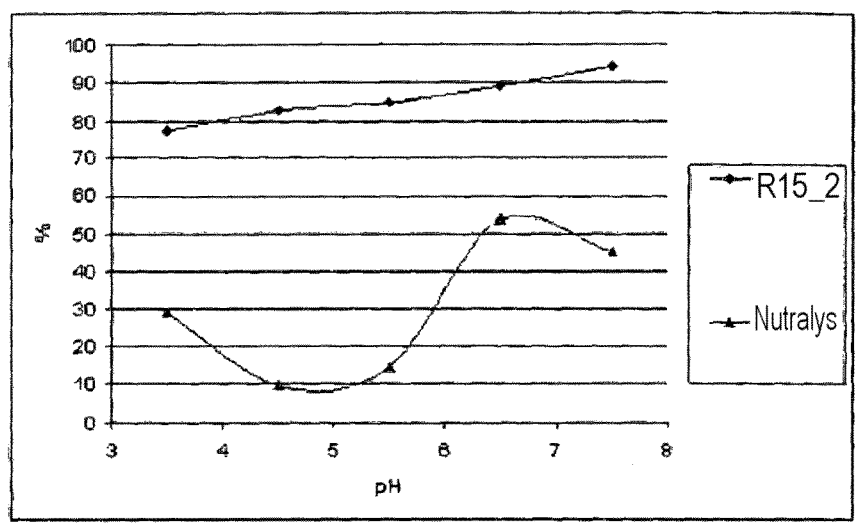
FIG. 2 graphically compares the solubility of the disclosed invention with that of Nutralys® as a function of pH.

The solubility is considered to be equal to the solids of a supernatant from centrifugation (15 min at 3000 g) of a suspension at a given pH and prepared by homogenization of 5 g of product in 100 g of water. FIG. 2 represents the solubility of the two products as a function of the pH. The R15_2 fraction has a better solubility than the Nutralys® F85M. This better solubility is an advantage for the energy formulation sector in the sport field.

Example 5

The emulsifying capacity as a function of the pH of the spray-dried fraction R15_2 obtained in example 2 is measured. It was compared to that of a Nutralys® F85M pea protein isolate.

The emulsifying activity of the product is determined on the basis of the volume of emulsion remaining (as %) after dispersion in a water-oil mixture at a given pH and then centrifugation. The emulsifying activity of the product is determined on the basis of the volume of emulsion remaining (as %) after dispersion in a water-oil mixture at a given pH and then centrifugation according to the method of Yasumatsu et al. (1972) described by: Naczk M., Rubin L. J., Shahidi F., *Functional properties and phytate content of pea protein preparations*. Journal of Food Science, Volume 51, No. 5, 1986, p. 1245-1247.

Figure 3:
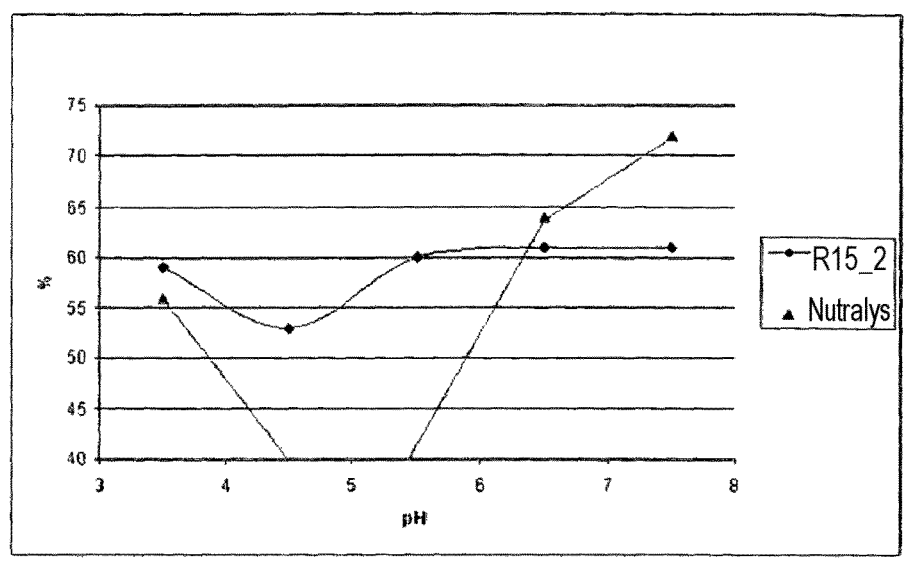
FIG. 3 graphically compares emulsifying capacity of the disclosed invention with that of Nutralys® prior art as a function of pH.
Figure 4:
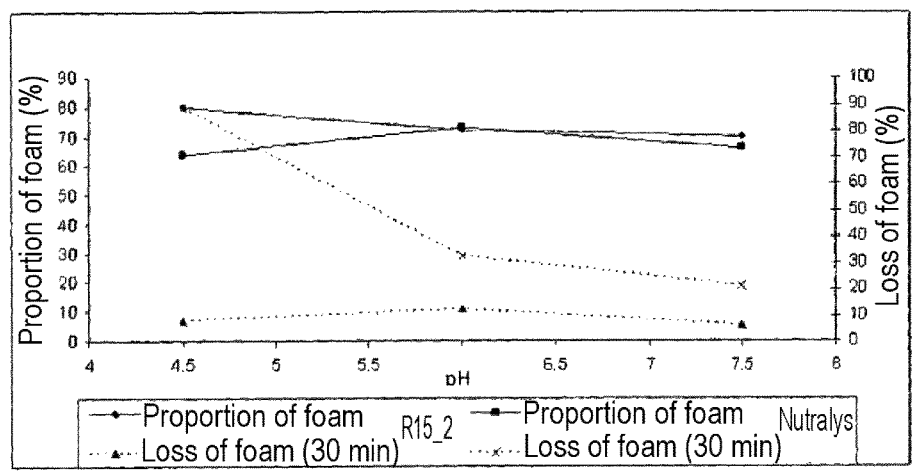
FIG. 4 graphically compares foaming capacity and the foam stability of the spray-dried fraction of R15-2 of Example 2 relative to Nutralys®.

FIG. 3 shows that, at pH 4.5 and 5.5, the R15_2 fraction has the best emulsifying capacity, the Nutralys® F85M having no emulsifying capacity at this pH. These emulsifying properties can be exploited, inter alia, in the pork meat field.

Example 6

The foaming capacity and the foam stability of the spray-dried fraction R15_2 obtained in example 2 is measured at various pHs. It is compared to that of a Nutralys® F85M pea protein isolate (see FIG. 4).

The foaming capacity of a sample of proteins is determined according to the method of Sumner A. K., Nielsen M. A., Youngs C. G., Production and evaluation of pea protein isolate. Journal of Food Science, Volume 46, 1981, p. 364-372. The loss of foam obtained is calculated from the percentage decrease in foam volume after being left to stand for 30 minutes.

The retention of the foam of the R15_2 fraction is much better than that of the Nutralys® F85M. In ice creams, meringues, fruit cakes, bread or high-protein bars, a better foam retention will actually be sought.

Example 7

The organoleptic qualities of the spray-dried fraction R15_2 obtained in example 2 are evaluated by a group of 20 panelists. They are compared to that of a Nutralys® F85M pea protein isolate.

For each test, 5 g of product are mixed with 150 ml of water and kept in a water bath at 50° C.

The R15_2 fraction is more neutral in terms of odor and taste in comparison with Nutralys® F85M.

Table 7.1 lists the descriptors proposed by the panelists during the analysis.

TABLE 7.1

|  | R15_2 | Nutralys ® F85M |
|---|---|---|
| Odor | Neutral, virtually neutral | Vegetable, fermented |
| Taste | Neutral to almost neutral | Bitter |

Example 8

The industrial stream of a part of the pea solubles pre-concentrated to 10% of solids (SOPPr) is diverted from the final concentration steps intended to bring it to 28% of solids in order to feed a pilot circuit, composed:

of a Westfalia® CA-505 centrifugal decanting unit adjusted to an acceleration of 3600 g and fed at approximately 12 m³/h. Said unit continuously generates 11 m³/h of an overflow fraction (OVF), reintroduced into the soluble-concentrating circuit downstream of the point where the SOPPr fraction is withdrawn, and 600 kg/h of sediment (SED) mixed with the protein isolate before drying;

of an ultrafiltration unit equipped with Kerasep® BW ceramic membranes sold by the company Novasep and having a cut-off threshold of 5 kDa (19 channels of 3.5 mm). Said unit is fed batchwise with a fraction of the volume of overflow (OVF) generated by the previous step.

The retentate fraction is maintained in total recycling on the feed and the permeate is discharged. The feed is supplemented with a permanent flow of water in a proportion of one volume of water for 5 volumes of permeate discharged. Throughout the filtration, the temperature is regulated at 60° C. and the transmembrane pressure is maintained at a value of between 2 and 3 bar. 2 fractions are generated: retentate (RET) and permeate (PERM).

The composition of the various fractions is given in Tables 8.1 and 8.2.

TABLE 8.1

|  | SOPPr | OVF | SED |  |
|---|---|---|---|---|
| Solids content | 10 | 8 | 25 | g/100 g |
| Protein content (N × 6.25) | 30 | 29 | 72 | g/100 g of solids |
| Ash content | 13 | 14 | 4 | g/100 g of solids |
| Total carbohydrate content | 44 | 45 | 12 | g/100 g of solids |
| Raffinose | 5 | 4 | — | g/100 g of solids |
| Stachyose | 14 | 13 | — | g/100 g of solids |
| Verbacose | 13 | 15 | — | g/100 g of solids |
| Others | 13 | 12 | 12 | g/100 g of solids |

TABLE 8.2

|  | RET | PERM |  |
|---|---|---|---|
| Solids content | 14 | 5 | g/100 g |
| Protein content (N × 6.25) | 84 | 3 | g/100 g of solids |
| Ash content | 5 | 19 | g/100 g of solids |
| Total carbohydrate content | 3 | 61 | g/100 g of solids |
| Raffinose | — | 5 | g/100 g of solids |
| Stachyose | — | 18 | g/100 g of solids |
| Verbacose | — | 20 | g/100 g of solids |
| Others | 8 | 17 | g/100 g of solids |

Example 9

Figure 5:
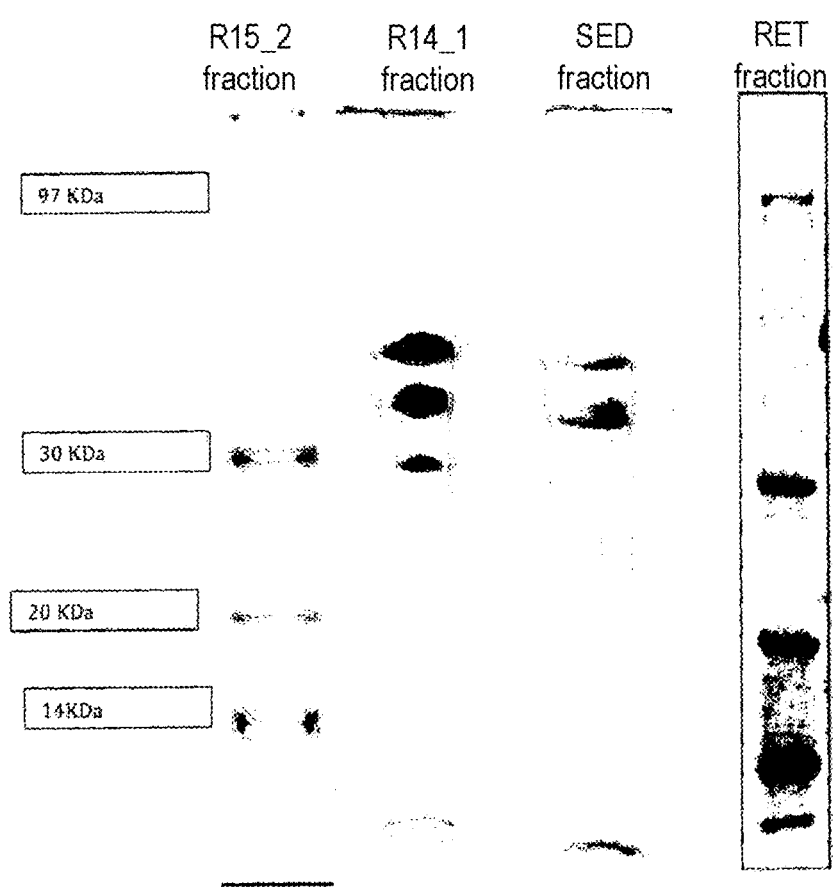
FIG. 5 illustrates the electrophoretic profile of the process fractions.

An electrophoretic profile, presented in FIG. 5, is determined on the spray-dried fraction R15_2 obtained in example 2, the R014_1 fraction obtained in example 1, and the SED and RET fractions obtained in example 8. The profile is produced by migrating the sample under denaturing and reducing conditions through a 20% polyacrylamide gel, followed by staining with Coomassie blue. The corresponding profiles appear in FIG. 5.

For the R15_2 and RET fractions, the marked presence of bands around 14 kDa corresponding to the albumins PA1 is noted, the band at 30 kDa corresponding to the albumin dimers PA2. This is in fact a fraction that is particularly advantageous for being exploited according to the indications of document FR 2 778 407 A1.

For the R014_1 and RET fractions, a predominance of bands at around 50 kDa and above is noted, reflecting the considerable presence of globulins, which enables it to be exploited, inter alia, in animal feed.

Example 10

This example illustrates the beneficial effect of the pretreatment of the solubles on the duration of the cycles and therefore of the availability of the concentrating step.

The operation of the centrifugal decanting unit described in example 8 is kept constant so as to observe the impact on the operating cycle duration of the soluble-concentrating step. The data are thus compared to those of this concentrating step without pretreatment of the solubles by the decanting unit. In the two situations, the parameters with which the concentrating system is operated (steam flow rate, vacuum, temperature produced, inlet and outlet solids of the solubles) are kept constant. The cycle duration is defined by the period of time which elapses between two interruptions of the evaporation system for washing. Washing was initiated as soon as the evaporation condensate flow rate decreased by more than 15% relative to its nominal value obtained after complete cleaning (>40 m$^3$/h for a soluble-feed flow rate of 55 m$^3$/h).

TABLE 10.1

|  |  | Cycle duration (h) |
|---|---|---|
| Without pretreatment of the solubles concentrated | Cycle 1 | 72 |
|  | Cycle 2 | 65 |
|  | Cycle 2 | 68 |
| With pretreatment of the solubles concentrated | Cycle 1 | 86 |
|  | Cycle 2 | 90 |
|  | Cycle 3 | 89 |

The invention claimed is:

1. A method for treating pea soluble fractions, comprising:
    a) a soluble fractions preparation step comprising
        (i) preparing a starch milk, by mixing pea flour and water in a kneading machine,
        (ii) extracting the starch and the fibers from said milk to obtain a protein-rich product,
        (iii) flocculating said protein-rich product,
        (iv) isolating through centrifugal decantation carried out on the product obtained from step iii) a highly protein-rich composition called a floc and a supernatant called soluble fractions,
    b) microfiltering or centrifuging said soluble fractions to obtain a microfiltration permeate and a microfiltration retentate or a centrifugation supernatant,
    c) ultrafiltering one of said microfiltration permeate and centrifugation supernatant to obtain an albumin-rich ultrafiltration permeate and an ultrafiltration retentate rich in PA1b fraction,
    d) subjecting said ultrafiltration permeate to reverse osmosis to obtain one of a reverse osmosis permeate enriched in PA1b fraction and a reverse osmosis retentate, and
    e) reintroducing all or part of said microfiltration permeate, microfiltration retentate, ultrafiltration retentate, and reverse osmosis retentate to the floc, downstream of the centrifugal decanting step.

2. The method as claimed in claim 1, wherein said soluble fraction is microfiltered by tangential membrane microfiltration.

3. The method as claimed in claim 2, wherein the tangential membrane microfiltration is carried out with ceramic membranes having a porosity of 0.01 μm to 1 μm.

4. The method as claimed in claim 1, wherein said microfiltering or centrifuging step b) is preceded by flocculation of insoluble particles contained in the pea soluble fraction.

5. The method as claimed in claim 1, wherein said soluble fraction is ultrafiltered using membranes which have a cut-off threshold of between 0.1 and 0.5 μm, at a transmembrane pressure maintained below 4 bar.

6. The method as claimed in claim 1, wherein the reverse osmosis is carried out with membranes having a cut-off threshold of between 100 Da and 500 Da.

7. The method as claimed in claim 2, wherein the tangential membrane microfiltration is carried out with ceramic membranes having a porosity of 0.05 μm to 0.5 μm.

8. The method as claimed in claim 2, wherein flocculation of insoluble particles contained in the pea soluble fraction is performed prior to microfiltering.

9. The method as claimed in claim 3, wherein flocculation of insoluble particles contained in the pea soluble fraction is performed prior to microfiltering.

10. The method as claimed in claim 2, wherein the ultrafiltering is carried out using membranes which have a cut-off threshold of between 0.1 and 0.5 μm, and a transmembrane pressure maintained below 4 bar.

11. The method as claimed in claim 3, wherein ultrafiltering is carried out using membranes which have a cut-off threshold of between 0.1 and 0.5 μm, the transmembrane pressure being maintained below 4 bar.

12. The method as claimed in claim 4, wherein ultrafiltering is carried out using membranes which have a cut-off threshold of between 0.1 and 0.5 μm, the transmembrane pressure being maintained below 4 bar.

* * * * *